United States Patent
Schöne

(10) Patent No.: US 6,175,055 B1
(45) Date of Patent: Jan. 16, 2001

(54) BENTONITE AS ODOR CONTROL MATERIAL

(75) Inventor: Rainer Walter Schöne, Königstein (DE)

(73) Assignee: The Procter & Gamble Company, Cincinnati, OH (US)

(*) Notice: Under 35 U.S.C. 154(b), the term of this patent shall be extended for 0 days.

(21) Appl. No.: 09/100,579

(22) Filed: Jun. 19, 1998

Related U.S. Application Data

(63) Continuation-in-part of application No. 08/793,374, filed as application No. PCT/US95/10864 on Feb. 24, 1997, now abandoned.

(51) Int. Cl.[7] ............................................. A61F 13/15
(52) U.S. Cl. .................................... 604/360; 604/368
(58) Field of Search .............................. 604/359, 368, 604/360

(56) References Cited

U.S. PATENT DOCUMENTS

| | | | |
|---|---|---|---|
| 3,935,363 | * | 1/1976 | Burkholder et al. .................. 442/116 |
| 4,494,482 | * | 1/1985 | Arnold ....................................... 119/1 |
| 4,500,670 | * | 2/1985 | McKinley et al. ..................... 524/445 |
| 4,535,098 | * | 8/1985 | Evani et al ............................ 521/149 |
| 4,795,482 | * | 1/1989 | Gioffre et al. ............................ 55/75 |
| 4,842,593 | * | 6/1989 | Jordan et al. ......................... 604/360 |
| 5,013,335 | * | 5/1991 | Marcus ...................................... 55/70 |
| 5,114,893 | * | 5/1992 | Hughes ................................. 501/149 |
| 5,407,879 | * | 4/1995 | Kajita ...................................... 502/62 |
| 5,628,736 | * | 5/1997 | Thompson ............................ 604/366 |

* cited by examiner

*Primary Examiner*—Dennis Ruhl
(74) *Attorney, Agent, or Firm*—Edward J. Milbrada; Jeffrey V. Bamber; Steven W. Miller

(57) ABSTRACT

An absorbent article, such as a pantiliner, has incorporated therein an unactivated bentonite clay as an odor control material for decreasing odors associated with bodily fluids.

12 Claims, 1 Drawing Sheet

BENTONITE AS ODOR CONTROL MATERIAL

This is a continuation-in-part of U.S. patent application Ser. No. 08/793,374, filed Feb. 24, 1997, now abandoned, which is a 371 of PCT/US95/10864 which is the PCT filing of European application 94306402.2 filed on Aug. 31, 1994.

This invention relates to an absorbent article for absorbing bodily fluids comprising an odour control material.

Absorbent articles are designed to be worn by humans to absorb bodily fluids, such as urine, menstrual fluid and perspiration, etc. Examples of absorbent articles include sanitary napkins, pantiliners, disposable diapers, incontinence pads, tampons and the like.

In use, the absorbent articles are known to acquire a variety of compounds, for example volatile fatty acids (e.g. isovaleric acid), ammonia, amines (e.g. triethylamine), sulphur containing compounds (e.g. mercaptans, sulphides), alcohols, ketones and aldehydes (e.g. furaldehyde) which release unpleasant odours. These compounds may be present in the bodily fluid or may be produced by fermentation once the bodily fluid is absorbed into the pad. In addition bodily fluids can contain microorganisms that can also generate malodorous byproducts. Unpleasant odours which emanate from absorbent pads when in use may make the wearer feel self conscious.

An object of the present invention is to provide an absorbent article providing odour control using a material which can be handled easily in production of an absorbent article, and is not expensive.

It has been found that bentonite clays have odour control properties when incorporated in absorbent articles.

The present invention provides an absorbent article having incorporated therein an odour control material for decreasing odours associated with bodily fluids, the odour control material comprising at least 50% by weight, preferably at least 80% by weight, of a bentonite clay.

According to one embodiment the absorbent article includes a bentonite clay as the only odour control material.

A number of odour control materials have previously been suggested for use in absorbent articles which, although efficient at odour control, are very expensive. Examples are carbon black and zeolites. The advantage of bentonite clays is that, on the one hand, they are effective as odour control materials and, on the other hand, they are readily available and relatively cheap. Accordingly, relatively large amounts of bentonite clay can be included in an absorbent article without substantially increasing the cost. Thus, whilst it may be necessary to use more bentonite as an odour control material in an absorbent article than, for example, carbon black or zeolite, the equivalent degree of odour control can be achieved more cheaply by use of bentonite.

The fact that more bentonite is used than, for example, carbon black or zeolite for an equivalent odour control effect is itself an advantage. Thus the requirements for production equipment and process control are less stringent, for bentonite than is the case for carbon black or zeolite where small amounts of materials have to be metered accurately into each product. In addition, as well as being an odour control material, bentonite is also an absorbent and, when incorporated into an absorbent article in the quantities appropriate for odour control, it can also supplement the absorbent capacity of the product. Finally, in contrast to carbon black or zeolite, bentonite is a naturally occurring mineral and may thus have better acceptability to consumers in the context of absorbent products such as sanitary products.

Any suitable bentonite clay with odour control properties can be used according to the invention. Examples include:

calcium bentonite, for example in granular form
sodium bentonite.

Preferably, the bentonite clays of the present invention comprise at least about 90% montmorillonite. More preferably, the clays comprise at least about 95% montmorillonite.

It is particularly preferred to use such calcium or sodium bentonite in the unactivated state. As is known in the art, clays may be activated by either heat treatment or acid treatment. As used herein, a bentonite clay is "unactivated" if it can be provided using such relatively simple processing steps, as mining, drying to remove at least some of the loosely held (not structural) water, grinding, and sizing (e.g. agglomeration and/or screening) without an acid treatment or heat treatment (beyond what may be necessary to dry the clay). As noted above, a particular benefit of the unactivated bentonite clays of the present invention is their low cost. One contributor to this low cost is the clays of the present invention do not require an activation process step to be effective as odor absorbers. An exemplary unactivated calcium bentonite is the granular calcium bentonite available from Laviosa Chimica Mineraria SpA as DETERCAL G IF. Such unactivated calcium bentonites are mined, dried, ground, and agglomerated prior to shipment. An exemplary unactivated sodium bentonite is available from ABI, Inc. of Palatine, IL as AP BASE CLAY. Such unactivated sodium bentonites are mined, dried and sized prior to shipment.

The absorbent article according to the invention may be a sanitary napkin, a pantiliner a disposable diaper, an incontinence pad, tampon or the like. According to one aspect of the invention the absorbent article is a pantiliner. According to another aspect of the invention the absorbent article is a sanitary napkin.

The amount of bentonite clay which may be used in the absorbent article as an odour control material can be readily determined by the skilled person bearing in mind the size of the absorbent article in question. For example, a suitable quantity of bentonite clay which may be used in a pantiliner, is from about 0.25 to 2.0 g, preferably the quantity is from about 0.5 to 1.5 g.

The absorbent article may be of conventional construction and may include other conventional components such as antimicrobial agents and ionic absorbents, for example absorbent gelling material (AGM). The quantity of AGM which may be added may also readily be determined by the skilled person for each absorbent article. For example about 0.05 to 0.7 g, preferably about 0.1 to 0.5 g, AGM may be appropriate for adding to a pantiliner.

The bentonite clay as an odour control material may be incorporated into the absorbent article by methods known in the art, for example the clay may be layered on the core of the absorbent material or mixed within the fibres of the absorbent core. The odour control material is preferably incorporated between two layers of cellulose tissue and, optionally, the material may be bonded between two cellulose tissue layers with, for example, a hot melt adhesive or any suitable bonding system. For example the odour control material may be incorporated in a layered structure in accordance with WO 94/01069 or Italian Patent Application TO 93A 001028.

The invention will now be illustrated with reference to the detailed description and examples taken in conjunction with the accompanying Figures.

An absorbent article, namely a pantiliner, which is an exemplary embodiment of an article according to the invention, is shown in cross section in FIGS. 1 to 4.

Figure 1:
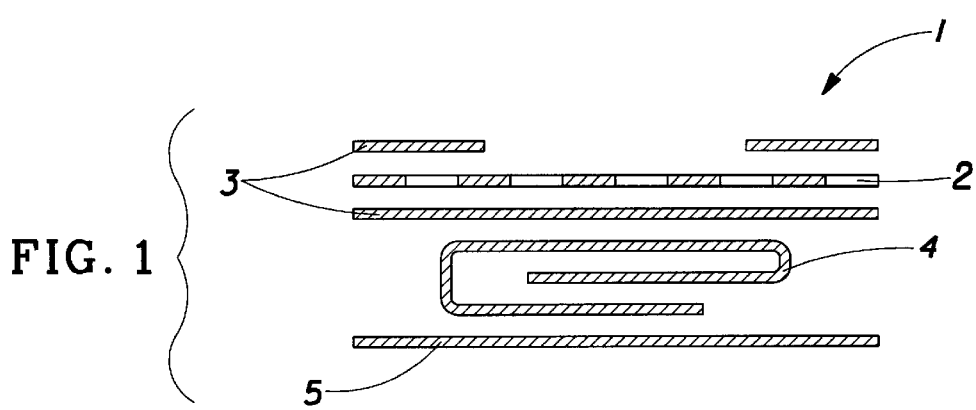
FIG. 1 shows a schematic cross section of a commercially available pantiliner is namely the Always Comfort Pantiliner (Always is a registered trade mark).
Figure 2:
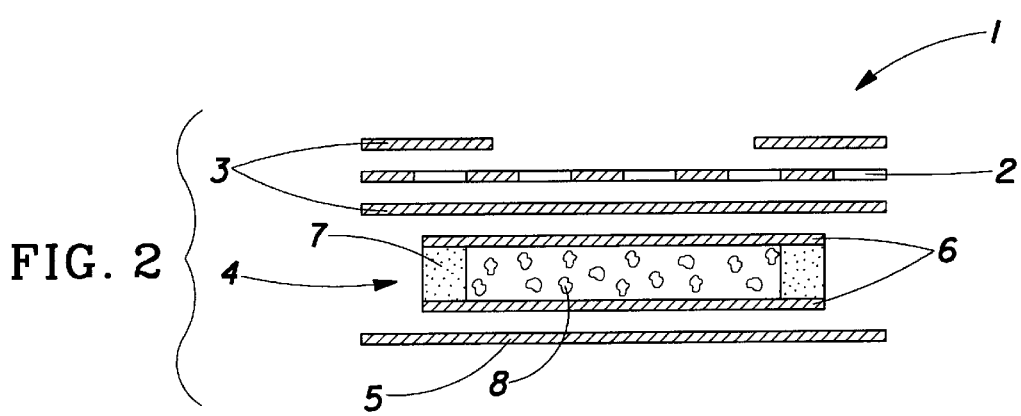
FIG. 2 shows a schematic cross section of the pantiliner of FIG. 1 with odour control material incorporated therein.

The pantiliner may be of any shape known in the art, for example, rectangular, hour glass, winged, etc. As shown in FIGS. 1 and 2 pantiliner 1 comprises a liquid pervious topsheet 2, a secondary top sheet 3, an absorbent core 4 and a liquid impervious backsheet 5. It is not, however, intended that the pantiliner according to the invention should be limited to embodiments comprising all such elements or additional elements may also be included.

The topsheets 2 and 3 are liquid permeable and, when pantiliner 1 is in use, are in close proximity to the skin of the user. The topsheets 2 and 3 are compliant, soft feeling and non-irritating to the user's skin and can be made from any of the conventional materials for this type of use. Non-limiting examples of suitable materials that can be used as the topsheets 2 and 3 are woven and nonwoven polyester, polypropylene, nylon and rayon and formed thermoplastic films.

Formed films are preferred for topsheet 2. Suitable formed films are described in U.S. Pat. No. 4324246, U.S. Pat. No. 4324214, U.S. Pat. No. 4341217 and U.S. Pat. No. 4463045. Secondary topsheet 3 is preferably a non-woven, more preferably an air through non-woven with a basis weight of 21 $g/m^2$, the non-woven being a bi-component web comprising polyester and polyethylene fibres in a mixture such as disclosed in WO 93/09744.

Formed films are preferred for topsheet 2 because they are pervious to liquids and yet non-absorbent. Thus, the surface of the formed film, which is in contact with the body, remains dry and is more comfortable to the wearer. The topsheet may be constituted by a covering structure for sanitary products such as described in EP-A-0 207 904. Preferably, the topsheet 2 is made of polyethylene perforated film (24.5 $g/m^2$).

The inner surface of secondary topsheet 3 may be secured in contacting relation to absorbent core 4. This contacting relationship results in liquid penetrating the topsheet 3 faster than if it were not in contact with absorbent core 4. Topsheet 3 can be maintained in contact with the absorbent core 4 by applying adhesive, preferably in spaced limited areas. Examples of suitable adhesives used for such purpose include the acrylic emulsion E-1833BT manufactured by the Rohm & Haas Company, Philadelphia, Pa. and the acrylic emulsion WB 3805 manufactured by H. B. Fuller Company of St. Paul, Minn. The adhesives can be applied by any technique, for example, the adhesive may be applied by spraying, by padding or by the use of transfer rolls. The adhesive may be in the form of a uniform continuous layer, a patterned layer of adhesive, or an array of separate lines, spirals or spots of adhesive. The absorbent core 4 is preferably secured in contacting relation to secondary topsheet 3.

Referring again to FIGS. 1 and 2, it can be seen that absorbent core 4 is positioned between secondary topsheet 3 and backsheet 5. Absorbent core 4 provides the absorptive means for absorbing the bodily fluid. Absorbent core 4 is generally compressible, conformable and non-irritating to the user's skin. It can comprise any suitable material for such purpose. Examples of such materials include multiple plies of creped cellulose wadding, fluffed cellulose fibres, wood pulp fibres, also known as airfelt, textile fibres, a blend of fibres, a mass or batt of fibres, a web of polymeric fibres, a blend of polyester and polypropylene fibres, layers of cellulose tissue or layers of air laid tissue.

Preferably, the core comprises a mass or batt of fibres. While many types of fibres may be used, a preferred material is a batt of polyester fibres. More preferably the core comprises cellulose tissue (63 $g/m^2$) which forms three absorbent layers. FIG. 1 shows an absorbent core 4 formed by one layer of cellulose tissue which has been folded as shown. FIG. 2 shows an absorbent core comprised of two layers of air laid cellulose tissue 6 joined at their longitudinal edges with adhesive 7.

Figure 3:
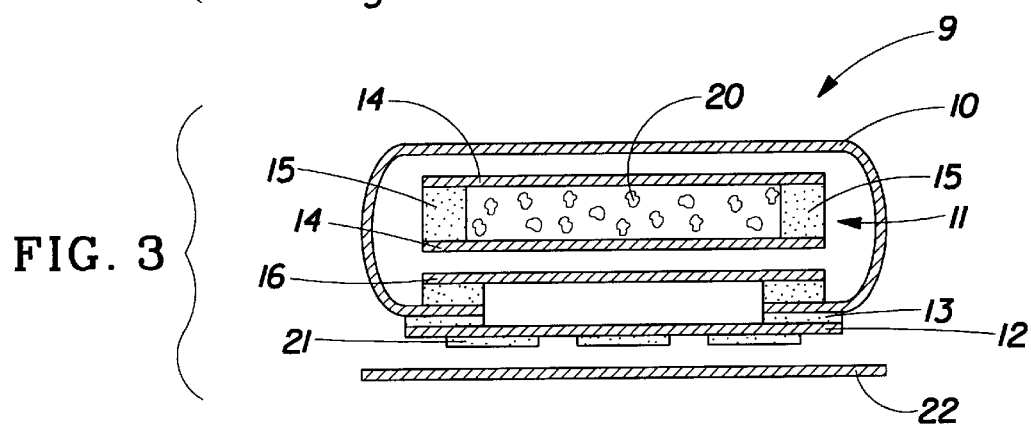
FIG. 3 shows a schematic cross section of a pantiliner having an absorbent core comprising three cellulose tissue layers, an odour control material being incorporated between the first and second tissue layers.
Figure 4:
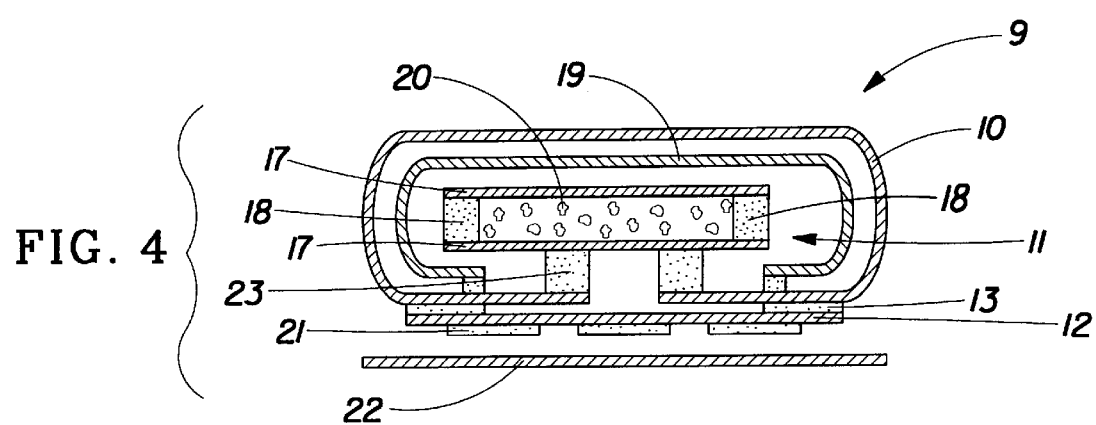
FIG. 4 shows a schematic cross section of a pantiliner having an absorbent core comprising three cellulose tissue layers, an odour control material being incorporated between the second and third tissue layers.

Preferably, the bentonite clay as an odour control material is incorporated into the absorbent core. It may, for example, be layered on the absorbent core or mixed with the fibres of the core. More preferably, the odour control material 8, 20 is layered in accordance with the teaching of WO 94/01069 or Italian Patent Application TO 93A 001028 between two layers of air laid cellulose tissue and the laminate is as shown in FIGS. 2 to 4 above. In particular, polyethylene powder, as thermoplastic material, may be mixed with bentonite clay as an odour control material and AGM and the mixture heated such that the polyethylene melts and glues the laminate layers and components together. Polyethylene powder is preferably also placed on the edges of the laminate as shown as 7, 15 and 18 in the Figures to ensure that edges of the laminate stick together and any loose odour control material or AGM does not fall out of the laminate.

As shown in FIGS. 3 and 4, pantiliner 9 comprises a liquid pervious topsheet 10, an absorbent core 11, a liquid impervious backsheet 12, adhesive 13 which fastens the topsheet 10 to the backsheet 12, a layer of adhesive 21 which is secured to the backsheet 12 and which is covered by removable release liner 22. The removable release liner 22 and associated adhesive 21 may also be included in the pantiliners of FIGS. 1 and 2. In FIG. 4 adhesive 23 in addition fastens the absorbent core 11 to the topsheet 10. It is not, however, intended that the pantiliner should be limited to embodiments comprising all such elements or additional elements may also be included.

Topsheet 10 is liquid permeable and, when pantiliner 9 is in use, is in close proximity to the skin of the user. The topsheet 10 is as described for topsheet 2 in FIGS. 1 and 2. The inner surface of topsheet 10 may be secured in contacting relation to absorbent core 11 as described for the pantiliner of FIGS. 1 and 2. Preferably, the topsheet 10 wraps around the core 11, as shown in FIGS. 3 and 4, and is fastened by means of an adhesive 13 to backsheet 12.

Referring again to FIGS. 3 and 4, it can be seen that absorbent core 11 is positioned between topsheet 10 and backsheet 12. Absorbent core 11 is as described for FIG. 2. FIG. 3 shows an absorbent core comprised of two layers of air laid cellulose tissue 14 joined at their longitudinal edges with adhesive 15 and having a layer of cellulose tissue 16 therebeneath to form a three layered absorbent core. FIG. 4 shows two layers of air laid tissue 17 joined at their longitudinal edges with adhesive 18 and having a layer of cellulose tissue 19 wrapped therearound to form the third layer of the absorbent core.

Referring to FIGS. 1 to 4, the pantiliner is provided with a backsheet 5, 12 which backsheet is impervious to liquids and, thus, prevents; menstrual fluid which may be expressed from absorbent core 4, 11 from soiling the body or clothing of the user. Suitable materials include woven and non-woven fabrics which have been treated to render them liquid repellent. Breathable or vapour pervious, liquid resistant materials, and those materials described in U.S. Pat. No. 3,881,489 and U.S. Pat. No. 3,989,867 can also be used. Preferred materials are those materials that are fluid and vapour impervious, because they provide additional fluid strikethrough protection. Especially preferred materials include formed thermoplastic films. One especially suitable material is a polyethylene film having a thickness of from about 0.075 mils to about 1.25 mils, with a 1.0 mil thickness polyethylene film being especially suitable. Preferably the backsheet 5, 12 is polyethylene embossed film (24.4 g/m$^2$).

The outer surface of backsheet 5, 12 may be coated with adhesive 21. Adhesive 21 provides a means for securing the pantiliner in the crotch portion of a panty. Any adhesive or glue suitable for such purpose can be used herein, with pressure sensitive adhesives being preferred. Suitable adhesives are Century A-305IV manufactured by the Century Adhesives Corporation and Instant Lok 34-2823 manufactured by the National Starch Company. Also, before pantiliner 1 or 9 is placed in use, the pressure sensitive adhesive 21 should be covered with removable release liner 22 in order to keep adhesive 11 from drying out or sticking to a surface other than the crotch portion of the panty prior to use. Any suitable release liner can be used for this purpose and such release liners are commercially available. Non-limiting examples of suitable release liners are BL 30 MG-A Silox EI/O and BL 30 MG-A Silox 4 P/O both of which are manufactured by the Akrosil Corporation. Preferably the release liner is a silicon paper having a thickness of about 45 $\mu$m (43.5 g/m$^2$). Other means which are known in the art may be used to affix the pantiliner in the crotch portion of a panty. FIGS. 3 and 4 show an embodiment which comprises the adhesive 21 and removable release liner 22.

The backsheet 5, 12 is preferably secured to the absorbent core 4, 11 by securement means (not shown), such as those well known in the art. Suitable securement means are the same means hereinbefore disclosed with respect to securing the secondary top sheet 3 to absorbent core 4.

The invention will now be illustrated with reference to the examples wherein the article for absorbing bodily fluids is a pantiliner or a sanitary napkin. It will, of course, be appreciated that other absorbent articles may also have the odour control material incorporated therein, the incorporation of the odour control material into the pantiliner may be achieved by other known methods and the odour control material may be any of those disclosed in the present specification.

EXAMPLE

Incorporation of the odour control material into a pantiliner.

The pantiliners used in the following examples were Always COMFORT Pantiliners (Always is a Registered Trade Mark) as sold by the Procter & Gamble Company. Each pantiliner was opened at one end. The inner cellulose tissue sheet, which constitutes the absorbent core of the product, was substituted with two layers of cellulose tissue that incorporate the odour control material homogeneously dispersed therein as shown in FIG. 2. The whole pantiliner structure was then reconstituted.

Samples were prepared by the method as described above, which samples incorporate bentonite clay as odour control material (OCM) as described herein.

Product 1 included DETERCAL G 1F (granular calcium bentonite available from Lavisoa Chimica Mineraria, Livorno, Italy) in an amount of 0.75 g/pantiliner.

Product 2 included AP BASE CLAY (sodium bentonite available from ABI, Inc., Palatine, Ill., USA) in an amount of 0.75 g/pantiliner.

A commercially available Always (Always is a Registered Trade Mark) pantiliner without modification was used as a reference.

Odour Control Test Protocol

Each test comprises four separate stages which may be summarised as follows:

a) Consignment of the products.

b) Product return and preparation of the test samples.

c) Sniff-test.

d) Statistical analysis of the Data.

Each stage is described in more detail below.

a) Women were chosen who were known to have an odour control problem. Each of five women selected was given a sample of each product individually packaged in an anonymous bag. Each product was worn for seven hours.

b) The used product was placed into an aluminum tray, approximately 1 cm deep, covered with a perforated aluminum sheet, in order to keep it out of view, and finally covered with another tray of the same type, which was kept thereon in inverted position up to the moment of the sniff-test.

c) The sniff-test was performed in a pre-ventilated room by five graders. Each grader had been preselected for their sensitivity to the unpleasant smells present in an absorbent article after use and their ability to grade the unpleasantness of the odour in a consistent manner. Every grader evaluated the odour of samples representing each of the products using a pleasantness scale which ranges from −10 (highest level of unpleasantness) to 5 (most pleasant). The pleasantness values for each product were obtained as a mean of 5 observations (five graders, one sample for each product).

d) The results collected from the test were then analyzed by statistical analysis software (SAS). The data was processed in order to show statistically significant differences between the treated and untreated products. This difference is shown in the table by means of a letter in the "Sig. Diff."(significant difference) column; results with the same letter are not significantly different. The standard for a significant difference is that of the Student's two tailed "t" test for comparison of data between two types of sample. Values of $p<0.05$ are considered statistically significant.

Results

The results are shown in the following table:

| PRODUCT | SCORE | SIG. DIFF. |
|---|---|---|
| Product 1 | −1.9 | A |
| (0.75 g/sample Ca bentonite) | | |
| Reference | −3.7 | B |
| Product 2 | −1.6 | A |
| (0.75 g/sample Na bentonite) | | |
| Reference | −2.4 | B |

$p < 0.05$

These results show that bentonite clay has a substantial odour control effect with respect to the reference.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having incorporated therein an odour control material for decreasing odours associated with bodily fluids, wherein the odour control material consists essentially of an unactivated bentonite clay;

the odour control material is layered on an absorbent core; and the absorbent article is selected from the group consisting of sanitary napkins, pantiliners, disposable diapers, incontinence pads, and tampons.

2. An absorbent article according to claim 1 wherein the bentonite clay is selected from the group consisting of calcium bentonite or sodium bentonite.

3. An absorbent article according to claim 1 wherein said absorbent article also comprises an absorbent gelling material.

4. An absorbent article according to claim 1 wherein said absorbent article is a pantiliner.

5. An absorbent article according to claim 4 wherein said odour control material is used at a level of between about 0.25 and about 2.0 g of bentonite clay per article.

6. An absorbent article according to claim 5 wherein said odour control material is used at a level of between about 0.5 and about 1.5 g of bentonite clay per article.

7. An absorbent article having incorporated therein an odour control material for decreasing odours associated with bodily fluids, said absorbent article comprising:

a liquid pervious topsheet;

a backsheet joined to said topsheet; and an absorbent core disposed between said topsheet and said backsheet wherein said absorbent core comprises an odour control material, said odour control material consisting essentially of an unactivated bentonite clay and said odour control material is layered on said absorbent cores;

said absorbent article being selected from the group consisting of sanitary napkins, pantiliners, disposable diapers, incontinence pads, and tampons.

8. An absorbent article according to claim 7 wherein said absorbent article further comprises a secondary topsheet disposed between said topsheet and said absorbent core.

9. An absorbent article according to claim 7 wherein said topsheet comprises a formed thermoplastic film.

10. An absorbent article according to claim 8 wherein said topsheet comprises a formed thermoplastic film and said secondary topsheet comprises a bicomponent web.

11. An absorbent article according to claim 7 wherein said core further comprises absorbent gelling material.

12. An absorbent article according to claim 7 wherein said backsheet has a core surface and an opposed outer surface, an adhesive being disposed on said outer surface.

* * * * *

UNITED STATES PATENT AND TRADEMARK OFFICE
CERTIFICATE OF CORRECTION

PATENT NO.    : 6,175,055 B1
DATED         : January 16, 2001
INVENTOR(S)   : Schöne It is certified that error appears in the above-identified patent and that said Letters Patent is hereby corrected as shown below:

Column 2,
Line 22, please delete "IF" and insert therefor -- 1F --.

Column 5,
Line 29, please delete "EI/O" and insert therefor -- E1/O.

Column 8,
Line 14, please delete "cores" and insert therefor -- core --.

Signed and Sealed this

Twenty-eighth Day of January, 2003

JAMES E. ROGAN
*Director of the United States Patent and Trademark Office*